United States Patent
MacDonald et al.

(10) Patent No.: US 9,078,947 B2
(45) Date of Patent: Jul. 14, 2015

(54) COMPOSITION FOR FORMING A POROUS ABSORBENT STRUCTURE

(71) Applicant: Kimberly-Clark Worldwide, Inc., Neenah, WI (US)

(72) Inventors: John Gavin MacDonald, Decatur, GA (US); Peter B. Dulcamara, Jr., Neenah, WI (US); Dave A. Soerens, Neenah, WI (US); Thomas J. Falk, Dallas, TX (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 202 days.

(21) Appl. No.: 13/832,966

(22) Filed: Mar. 15, 2013

(65) Prior Publication Data

US 2014/0276513 A1 Sep. 18, 2014

(51) Int. Cl.
| | |
|---|---|
| *A61F 13/53* | (2006.01) |
| *A61L 15/42* | (2006.01) |
| *D06N 3/00* | (2006.01) |
| *A61L 26/00* | (2006.01) |
| *A61L 15/26* | (2006.01) |

(52) U.S. Cl.
CPC .............. *A61L 15/425* (2013.01); *A61F 13/53* (2013.01); *A61L 15/26* (2013.01); *A61L 26/0085* (2013.01); *A61L 26/0095* (2013.01); *D06N 3/0043* (2013.01); *D06N 3/0059* (2013.01); *D06N 3/0088* (2013.01); *A61F 2013/530496* (2013.01); *A61F 2013/530583* (2013.01); *A61F 2013/530708* (2013.01); *Y10T 428/249921* (2015.04); *Y10T 428/249986* (2015.04); *Y10T 442/2484* (2015.04)

(58) Field of Classification Search
CPC ... A61F 13/15; A61F 13/15707; A61F 13/47; A61F 13/4704; A61F 13/475; A61F 13/476; A61F 13/49; A61F 13/49004; A61F 13/49007; A61F 13/53; A61F 13/51478; A61F 13/56; B29C 4/00; A61L 15/18; A61L 15/60
USPC ........... 604/367, 368–370; 526/271, 277, 320
See application file for complete search history.

(56) References Cited

U.S. PATENT DOCUMENTS

| | | |
|---|---|---|
| 3,125,294 A | 3/1964 | Lill |
| 3,179,955 A | 4/1965 | Wade |
| 3,211,563 A | 10/1965 | Reed |
| 3,987,000 A | 10/1976 | Gleichenhagen et al. |
| 4,023,978 A | 5/1977 | Messina |
| D307,843 S | 5/1990 | Parshall |
| 5,140,017 A | 8/1992 | Pickford |
| 5,196,185 A | 3/1993 | Silver et al. |
| 5,359,735 A | 11/1994 | Stockwell |
| D363,214 S | 10/1995 | Parola et al. |

(Continued)

FOREIGN PATENT DOCUMENTS

| | | |
|---|---|---|
| DE | 10 2005 041 117 A1 | 3/2007 |
| EP | 0 149 249 A2 | 7/1985 |

(Continued)

*Primary Examiner* — Melanie Hand (57) ABSTRACT

A porous absorbent structure is disclosed which includes absorbent particles and a superabsorbent polymer material having less than about 1000 parts per million residual monoethylenically unsaturated monomer, the superabsorbent polymer material substantially coating the absorbent particles and connecting the particles into a porous network to form the porous absorbent structure.

24 Claims, 3 Drawing Sheets

(56) References Cited

U.S. PATENT DOCUMENTS

| | | |
|---|---|---|
| 5,853,802 A | 12/1998 | Boyer et al. |
| 6,216,920 B1 | 4/2001 | Baggett |
| 6,644,563 B2 | 11/2003 | Presson |
| 6,822,135 B2 | 11/2004 | Soerens et al. |
| 6,887,961 B2 | 5/2005 | Soerens et al. |
| 6,987,210 B1 | 1/2006 | Giloh |
| 7,425,589 B2 | 9/2008 | Girg et al. |
| 7,767,133 B2 | 8/2010 | Giloh et al. |
| 7,815,924 B2 | 10/2010 | Vonbehren et al. |
| 8,088,315 B2 | 1/2012 | Torres et al. |
| 8,096,979 B2 | 1/2012 | Lina et al. |
| 8,124,549 B2 | 2/2012 | Torres et al. |
| 8,148,598 B2 | 4/2012 | Tsang et al. |
| 2005/0186147 A1 | 8/2005 | Tamarkin et al. |
| 2006/0263586 A1 | 11/2006 | Lanthier et al. |
| 2007/0178144 A1 | 8/2007 | Hameyer et al. |
| 2008/0022940 A1 | 1/2008 | Kirsch et al. |
| 2009/0181070 A1 | 7/2009 | Blease et al. |
| 2009/0324506 A1 | 12/2009 | Seidling et al. |
| 2009/0324713 A1 * | 12/2009 | Ulman et al. ............... 424/464 |

FOREIGN PATENT DOCUMENTS

| | | |
|---|---|---|
| EP | 0 165 880 B1 | 11/1988 |
| EP | 1 952 687 A2 | 8/2008 |
| GB | 734181 A | 7/1955 |
| GB | 1 498 935 A | 1/1978 |
| WO | WO 95/06522 A1 | 3/1995 |
| WO | WO 96/04024 A1 | 2/1996 |
| WO | WO 03/059228 A2 | 7/2003 |
| WO | WO 2005/108669 A2 | 11/2005 |
| WO | WO 2011/143131 A1 | 11/2011 |

* cited by examiner

COMPOSITION FOR FORMING A POROUS ABSORBENT STRUCTURE

FIELD OF THE INVENTION

The present invention relates generally to the field of porous absorbent materials, and more specifically to porous absorbent particulate structures which may be sprayed onto a variety of surfaces.

BACKGROUND OF THE INVENTION

Good hygiene is a global need, and using disposable absorbent articles is frequently an easier and more hygienic way to meet this need. The term "absorbent article" generally refers to a device which can absorb and contain fluids. For example, personal care absorbent articles refer to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

Availability of absorbent articles can be limited in some areas due to the complex and costly manufacturing required for some absorbent articles. Necessary materials may not be locally available. Traditional disposable absorbent articles can include a topsheet, a backsheet, and an absorbent core positioned therebetween.

Alternate methods of forming disposable garments are also known. For example, garments formed by dipping and spraying are known in the art. U.S. Pat. No. 6,987,210 to Giloh discloses a disposable protective undergarment that may be formed by dipping a form into an elastic liquid permeable material. An absorbent pad may be attached to the dip-formed garment in the crotch area. The garment may be sprayed with adhesive so that cotton or other fibers may be attached to the interior of the garment. In another example, U.S. Pat. No. 8,124,549 to Torres discloses a composition for forming a fabric by spraying the composition onto a supporting surface. The composition includes fibers, a binder and a diluent. The composition may be sprayed directly onto a person to form a shirt or dress. In some embodiments, the composition may be sprayed over a wire frame positioned on a person so that the resulting garment has a particular shape. However, the composition disclosed in Torres is not sufficiently absorbent to function as a substitute or replacement for most commonly available absorbent articles.

There remains a need for articles that are both absorbent and easily manufactured in all regions of the world which have the integrity, coverage and absorbent capacity to meet the needs of the consumer.

SUMMARY OF THE INVENTION

The present invention is directed to a porous absorbent structure and a method of forming porous absorbent structures. In one embodiment, the method of forming a porous absorbent structure may include the steps of providing a superabsorbent polymer material having a viscosity of less than about 10,000 cps.

Absorbent particles including, but not limited to, organic absorbent particles may be added into the superabsorbent polymer material to form a mixture. The mixture may have a ratio by weight of superabsorbent polymer material to absorbent particles that is greater than 3:1 and, in some embodiments, greater than about 3.5:1 and less than about 6:1. Certain embodiments of the invention may include absorbent particles having an average ratio of length to width of less than about 5, and preferably less than about 3. The absorbent particles may have an average length of greater than about 20 microns and less than about 100 microns.

The mixture of superabsorbent polymer material and absorbent particles is sprayed onto a form, and the mixture is dried to produce a porous absorbent structure substantially conforming to the shape of the form. In some embodiment, the form may be at least a portion of a human body. The form may, however, also be a nonwoven material, a woven material, paper, a film or a combination thereof. The method of forming a porous absorbent structure may also include the step of removing the porous absorbent structure from the form.

In selected embodiments, the superabsorbent polymer material has less than about 1000 parts per million residual monoethylenically unsaturated monomer which may be an acrylic acid.

The porous absorbent structure in certain embodiments may formed by the process of providing a superabsorbent polymer material having a viscosity of less than about 10,000 cps and adding absorbent particles into the superabsorbent polymer material to form a mixture, wherein the ratio by weight of superabsorbent polymer material to absorbent particles in the mixture is greater than 3:1 and less than about 6:1. The mixture may be applied to a form and dried to produce a porous absorbent structure substantially conforming to the shape of the form.

The porous absorbent structure may include absorbent particles and a superabsorbent polymer material that substantially coats the absorbent particles and connects the absorbent particles into a porous absorbent network as shown in the figures. The ratio by weight of the superabsorbent polymer material to the absorbent particles in the porous absorbent structure may be greater than 1:1, and may be greater than 1.1:1 and in some embodiments may be less than 1.5:1. Such porous absorbent structures may have a Peak Stretch of at least about 10% and at least about 25% in certain embodiments. The porous absorbent structure may also have a Peak Energy of at least about 150 g/cm, and in some embodiments a Peak Energy of at least about 250 g/cm.

The present invention is also suitable for use as an absorbent wiper when the porous absorbent structure is attached to a material such as a nonwoven material.

The mixture of superabsorbent polymer material and absorbent particles may be applied directly, by spraying, pouring or other application method, to a nonwoven material to increase the absorbency of the nonwoven material.

An absorbent article may be formed using an outer cover adapted to be secured to a person, the outer cover having an inner side. A porous absorbent structure which includes absorbent particles and superabsorbent polymer material may be applied to the inner side of the outer cover. Alternately, a mixture of superabsorbent polymer material and absorbent particles may be sprayed onto the inner side of the outer cover, the porous absorbent structure being formed directly on the outer cover which may act as a form for the porous absorbent structure.

The superabsorbent polymer material in the porous absorbent structure may substantially coat the absorbent particles and connect the particles into a porous network. In selected embodiments, the ratio by weight of the superabsorbent polymer material to the absorbent particles in the porous absorbent structure is greater than 0.8:1 and less than 1.4:1.

DETAILED DESCRIPTION

Reference will now be made in detail to embodiments of the invention, one or more examples of which are illustrated in the figures. Each example is provided by way of explanation of the invention, and not meant as a limitation of the invention. For example, features illustrated or described as part of one embodiment, may be used with another embodiment, to yield still a further embodiment. It is intended that the present invention include modifications and variations to the embodiments described herein.

The present invention is directed to porous absorbent structures and methods for forming porous absorbent structures. An embodiment of the porous absorbent structure of the present invention is pictured in FIGS. 1-5. Porous absorbent structures according to the present invention include absorbent particles that are substantially coated with a superabsorbent polymer material or composition. The superabsorbent polymer material also connects the absorbent particles into a porous absorbent network. In such embodiments, the ratio by weight of the superabsorbent polymer material to the absorbent particles in the porous absorbent structure may be greater than 1:1 and less than about 1.5:1. In a preferred embodiment, the weight ratio of superabsorbent polymer material to the absorbent particles in the porous absorbent structure is 1.1:1. As used herein, the term "superabsorbent" refers to a water-swellable, water-insoluble organic or inorganic material capable, under the most favorable conditions, of absorbing at least about 10 times its weight or at least about 15 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent polymer material substantially covers the particles and binds them together. Selected embodiments of the present invention include a mixture of superabsorbent polymer material and absorbent particles which can be applied using a commonly available low cost hand spray bottle.

The particular embodiment shown in FIGS. 1-5 is formed from micronized cellulose particles in a superabsorbent polymer material. The mixture may be sprayed directly onto a spill or a part of a human body and, upon drying, becomes a porous absorbent composition. Once the porous absorbent composition has absorbed the spill or exudate, it can be removed and replaced, if desired. For example, the mixture may be applied directly to a wound. When the mixture dries into a porous absorbent structure, it absorbs exudate in the wound. The porous absorbent structure retains its integrity and may be removed from the wound without damaging the surrounding tissue. The porous absorbent structure of the present invention has sufficient integrity to maintain its shape and attachment to the form onto which it was sprayed.

Alternately, the mixture may be sprayed onto a low-cost commonly available substrate that may or may not have absorbent properties. The combination may be used as an absorbent garment or article such as a wipe. After the porous absorbent material has absorbed the exudate, the porous absorbent material can be easily removed from the substrate and the substrate re-used after application of additional mixture.

A method for forming such a porous absorbent structure includes providing a superabsorbent polymer material which, in selected embodiments, has a viscosity that permits delivery of the superabsorbent polymer material through a commonly available low cost conventional hand sprayer or spray bottle. In some embodiments, the viscosity of the superabsorbent polymer material is less than about 10,000 cP and greater than about 500 cP. In other embodiments, the viscosity of the superabsorbent polymer material is preferably less than 2,000 cP and more preferably less than 1000 cP. In some embodiments, the viscosity of the superabsorbent polymer material is greater than 500 cP, and in other embodiments greater than 650 cP. The viscosity of the superabsorbent polymer material is measured at 16 hours according to the test procedure outlined in U.S. Pat. No. 7,312,286. As explained therein, the viscosity of the superabsorbent polymer material is measured using a Brookfield DVII+ Programmable viscometer which is available from Brookfield Engineering, Middleboro, Mass., U.S.A. About 200-250 ml of the superabsorbent polymer material is taken in a 25-ounce plastic cup. The viscometer is generally zeroed initially with a desired Spindle. For the superabsorbent polymer material, Spindle Number 3 is used. The viscosity is measured at 20 RPM and at temperature of 22.±.1 degrees C.

A superabsorbent polymer material suitable for use in the present invention is described as a superabsorbent binder polymer solution in U.S. Pat. No. 6,849,685 to Soerens et al., U.S. Pat. No. 7,312,286 to Lang et al., and U.S. Pat. No. 7,335,713 to Lang et al., the entirety of each of these references is herein incorporated by reference. The superabsorbent binder polymer solution described therein is capable of post-application, moisture-induced crosslinking. Whereas most superabsorbent polymers require the addition of an internal crosslinker to reinforce the polymer, the superabsorbent polymer material used in the present invention does not require the addition of a crosslinking agent because the organic monomers act as an internal crosslinker. The internal crosslinker allows the superabsorbent polymer material to be formed by coating the water-soluble precursor polymer onto the substrate and then removing the water to activate the latent crosslinker.

Soerens et al., in U.S. Pat. No. 6,737,491, describes an absorbent binder composition that may be used as a superabsorbent polymer material in the present invention. The absorbent binder composition disclosed in Soerens et al. is a monoethylenically unsaturated polymer and an acrylate or methacrylate ester that contains an alkoxysilane functionality that is particularly suitable for use in manufacturing absorbent articles. Also described in Soerens et al. is a method of making the absorbent binder composition that includes the steps of preparing a monomer solution, adding the monomer solution to an initiator system, and activating a polymerization initiator within the initiator system reported an alcohol-based, water-soluble binder composition. "Monomer(s)" as used herein includes monomers, oligomers, polymers, mixtures of monomers, oligomers and/or polymers, and any other reactive chemical species which are capable of co-polymerization with monoethylenically unsaturated carboxylic, sulphonic or phosphoric acid or salts thereof. Ethylenically unsaturated monomers containing a trialkoxysilane functional group are appropriate for this invention and are desired. Desired ethylenically unsaturated monomers include acrylates and methacrylates, such as acrylate or methacrylate esters that contain an alkoxysilane functionality.

The superabsorbent binder polymer composition disclosed in the references noted above is the reaction product of at least 15 percent by mass monoethylenically unsaturated carboxylic, sulphonic or phosphoric acid or salts thereof, an acrylate or methacrylate ester that contains an alkoxysilane functionality which, upon exposure to water, forms a silanol functional group which condenses to form a crosslinked polymer, a copolymerizable hydrophilic glycol containing ester monomer; and/or, a plasticizer.

The monoethylenically unsaturated monomer is preferable acrylic acid. Other suitable monomers include carboxyl group-containing monomers: for example monoethylenically unsaturated mono or poly-carboxylic acids, such as (meth) acrylic acid (meaning acrylic acid or methacrylic acid; similar notations are used hereinafter), maleic acid, fumaric acid, crotonic acid, sorbic acid, itaconic acid, and cinnamic acid; carboxylic acid anhydride group-containing monomers: for example monoethylenically unsaturated polycarboxylic acid anhydrides (such as maleic anhydride); carboxylic acid salt-containing monomers: for example water-soluble salts (alkali metal salts, ammonium salts, amine salts, and the like) of monoethylenically unsaturated mono- or poly-carboxylic acids (such as sodium(meth)acrylate, trimethylamine(meth) acrylate, triethanolamine(meth)acrylate), sodium maleate, methylamine maleate; sulfonic acid group-containing monomers: for example aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl(meth)acrylate, 2-hydroxy-3-(meth)acryloxy propyl sulfonic acid]; sulfonic acid salt group-containing monomers: for example alkali metal salts, ammonium salts, amine salts of sulfonic acid group containing monomers as mentioned above; and/or amide group-containing monomers: vinylformamide, (meth)acrylamide, N-alkyl(meth)acrylamides (such as N-methylacrylamide, N-hexylacrylamide), N,N-dialkyl(meth)acryl amides (such as N,N-dimethylacrylamide, N,N-di-n-propylacrylamide), N-hydroxyalkyl(meth)acrylamides [such as N-methylol (meth)acrylamide, N-hydroxyethyl(meth)acrylamide], N,N-dihydroxyalkyl(meth)acrylamides [such as N,N-dihydroxyethyl(meth)acrylamide], vinyl lactams (such as N-vinylpyrrolidone).

Suitably, the amount of monoethylenically unsaturated carboxylic, sulphonic or phosphoric acid or salts thereof relative to the weight of the superabsorbent binder polymer composition may range from about 15 percent to about 99.9 percent by weight. The acid groups are desirably neutralized to the extent of at least about 25 mol percent, that is, the acid groups are preferably present as sodium, potassium or ammonium salts. The degree of neutralization is preferably at least about 50 mol percent.

One of the issues in preparing water-soluble polymers is the amount of the residual monoethylenically unsaturated monomer content remaining in the polymer. For applications in personal hygiene it is required the amount of residual monoethylenically unsaturated monomer content of the superabsorbent polymer composition be less than about 1000 ppm, and more preferably less than 500 ppm, and even more preferably less than 100 ppm. U.S. Pat. No. 7,312,286 discloses at least one method by which an absorbent binder composition may be manufactured so that the residual monoethylenically unsaturated monomer content is at least less than 1000 parts per million. The analysis of residual monoethylenically unsaturated monomer is determined according to the Residual Monoethylenically Unsaturated Monomer Test which is disclosed in U.S. Pat. No. 7,312,286. More specifically, the residual monoethylenically unsaturated monomer analysis is carried out using solid film obtained from the polymer solution or superabsorbent composition. By way of example for this test description, the monoethylenically unsaturated monomer is acrylic acid. High performance liquid chromatography (HPLC) with a SPD-IOAvp Shimadzu UV detector (available from Shimadzu Scientific Instruments, having a place of business in Columbia, Md., U.S.A) is used to determine the residual acrylic acid monomer content. To determine the residual acrylic acid monomer, about 0.5 grams of cured film is stirred in 100 ml of a 0.9% NaCl-solution for 16 h using a 3.5 cm L×0.5 cm W magnetic stirrer bar at 500 rpm speed. The mixture is filtered and the filtrate is then passed through a Nucleosil C8 100A reverse phase column (available from Column Engineering Incorporated, a business having offices located in Ontario, Calif., U.S.A.) to separate the acrylic acid monomer. The acrylic acid monomer elutes at a certain time with detection limit at about 10 ppm. The peak area of resulting elutes calculated from the chromatogram is then used to calculate the amount of residual acrylic acid monomer in the film. Initially, a calibration curve was generated by plotting the response area of pure acrylic acid elutes against its known amount (ppm). A linear curve with a correlation coefficient of greater than 0.996 was obtained.

Absorbent particles are added to the superabsorbent polymer material to form a mixture which has not yet been substantially cross-linked, but will result in a porous absorbent structure when cross-linking occurs. As used herein, the term "absorbent particles" generally refers to particles which can absorb and contain fluids.

The absorbent particles may be organic or inorganic. Suitable organic absorbent particles include but are not limited to cellulose, rice, wheat flour, teff, fava, almond nut flour, kenaf and corn starch. Suitable inorganic particles include but are not limited to Arizona sand, pumice, diatomaceous earth and chalk.

In selecting absorbent particles to use in the present invention, care must be taken to avoid increasing the cross-linking of the superabsorbent polymer material to a level sufficiently high so that the resulting material will be too brittle to maintain integrity and function properly as an absorbent material.

The size of the absorbent particles is preferably chosen to permit the particles to add sufficient absorbency to the porous absorbent material without interfering with the delivery method of the mixture. For example, certain fibers may clog a typical hand sprayer. Particles having an average ratio of length to width of less than about 5 are preferred. Even more preferred are absorbent particles having an average ratio of length to width of less than about 3. In many preferred embodiments, the absorbent particles have an average length of greater than about 20 microns and less than about 80 microns.

Absorbent particles may be added to the superabsorbent polymer material material (an aqueous solution of sodium polyacrylate available from Evonick Stockhausen, LLC under the designation "SR1717" or "Absorbent Binder A" which is manufactured in accordance with U.S. Pat. No.

7,312,286) so that the ratio by weight of superabsorbent polymer material to absorbent particles is greater than about 3:1, and in some embodiments is greater than or equal to 3.5:1. In selected embodiments the ratio by weight of superabsorbent polymer material to absorbent particles in the mixture is less than about 6:1. In certain embodiments, absorbent particles are added into the superabsorbent polymer material to form a mixture wherein the ratio by weight of superabsorbent polymer material to absorbent particles in the mixture is greater than 3:1 and less than about 6:1. Ratios within these ranges enable formation of porous absorbent structures with suitable integrity and absorbency.

After mixing the absorbent particles until they are dispersed in the superabsorbent polymer material and the desired weight ratio has been attained, other additives may be added to the mixture. For example, glycerol may be added to the mixture of superabsorbent polymer material and absorbent particles to increase the flexibility and elongation of the porous absorbent material. Other additives may be utilized to increase the flexibility and integrity of the porous absorbent material, as well as other properties. For example, some embodiments may include poly(ethylene glycol) (PEG) having a molecular weight of 8000 in an amount of approximately fifteen percent (15%) by weight.

The mixture may be poured or sprayed onto a desired form. In some instances, the mixture may be applied directly onto the area where the absorbent properties are needed. For example, the mixture may be sprayed directly onto a wound or onto another area of a human where absorbency is needed. In such examples, the form would be the person. Other forms useful in the present invention include paper, film, woven materials, nonwoven materials and combinations thereof. For example, the mixture may be applied to a nonwoven material to increase its absorbency and thereby enable the composite material to be used as a wiper for any number of surfaces including, but not limited to, skin. "Nonwoven" or "nonwoven web" refers to materials and webs or material having a structure of individual fibers or filaments which are interlaid, but not in an identifiable manner as in a knitted fabric. Nonwoven fabrics or webs have been formed from many processes such as, for example, meltblowing processes, spunbonding processes, air laying processes, and bonded carded web processes. In certain embodiments, a rigid form may be used to shape a porous absorbent structure, after which the porous absorbent structure may be removed from the form and used alone or as part of an absorbent article.

The absorbent capacity of the superabsorbent polymer material or composition alone should be at least one (1) gram of fluid per gram of superabsorbent polymer material, and in some embodiments at least three (3) grams of fluid per gram of superabsorbent polymer material, when measured using the Centrifuge Retention Capacity Test described in U.S. Pat. No. 7,312,286.

In selected embodiments, the retention capacity of the porous absorbent structure of the present invention is preferably greater than 10 g/g, and more preferably is greater than 12 g/g when measured using the Centrifuge Retention Capacity Test described in U.S. Pat. No. 7,312,286.

A number of samples were formed and test values for these samples are reported in Tables 1 and 2. The superabsorbent polymer material used in each of the samples was obtained from Evonik Stockhausen, LLC (Greensboro, N.C., U.S.A.) under the designation "SR1717" or "Absorbent Binder A", which is manufactured in accordance with U.S. Pat. No. 7,312,286. Absorbent Binder A is an aqueous solution of sodium polyacrylate. Two (2) grams of each of the substances listed in the tables was added to seven (7) grams of this superabsorbent polymer material and stirred for three minutes. For the alginate sample, two (2) grams of alginate was added to seven (7) grams of Absorbent Binder A. For the first sample listed in Table 1, no particles or other substance was added to superabsorbent polymer material. Each of the mixtures was poured into a commonly available round glass evaporation dish and set aside to dry for at least 20 minutes. The resulting porous absorbent structure conformed to the shape of the glass dishes.

In order to gauge the strength and toughness of the porous absorbent structures, a series of samples were subjected to tensile testing. An MTS Insight Electromechanical 1 kN Extended Length unit was used to conduct the testing with a 100N head (Model 820-1XLTEL/0060. MTS Systems Corp., Eden Prairie, Minn.). The samples were approximately 6 cm circles or squares. The thickness of each sample was also measured using a digital caliper. Test values reported in Tables 1 and 2 include Peak Load, Peak Stretch and Peak Energy. Peak Stretch is a measure of the ductility of a material and is determined in a tensile test. It is the increase in the length of the sample measured after rupture (that is, the length of the sample after rupture minus the original sample length) divided by original sample length. Higher elongation indicates higher ductility. Peak Energy is the energy absorbed by the sample up to the point of maximum load. For the samples reported in Tables 1 and 2, the maximum load corresponded to either failure (the energy the sample can absorb before failing) or an amount greater than 100N. Peak Load, as reported in the tables, is the highest value reached by the sample during a test.

The superabsorbent polymer material sample listed in Table 1 showed a reasonable balance of properties but lacked the appropriate concentration of particles which is necessary to achieve the present invention. The sample which included alginate powder showed less Peak Load than desired and lacked the particles necessary to enhance the absorbency of the material.

The almond nut shell powder formed a porous absorbent structure with less integrity than other absorbent particles, but was still satisfactory. A number of samples of porous absorbent structures in Table 1 were formed with flour (wheat flour (Pillsbury® Best All-Purpose Flour available from The J.M. Smucker Co, Orrville Ohio, U.S.A.), rice flour, teff flour and garbanzo bean and fava bean flour (all available from Bob's Red Mill, Milwaukee, Oreg., U.S.A.)), and corn starch (available from Pinnacle Foods Corp., Cherry Hill, N.J. U.S.A). All of the porous absorbent structures made with these particles demonstrated good integrity. The porous absorbent structure formed with kenaf particles demonstrated particularly good load characteristics, although peak stretch values were less than desired. However, glycerol may be added to the particles and superabsorbent polymer material when forming the porous absorbent structure to enhance the stretch and flexibility of the porous absorbent structure. Micronized cellulose was used to formed a porous absorbent structure, also reported in Table 1, that had good integrity.

TABLE 1

| Sample Description | Sample Thickness (mm) | Peak Load (gF) | Peak Stretch (%) | Peak Energy (g/cm) | Particle Size (μm) |
|---|---|---|---|---|---|
| Superabsorbent polymer material | 1.15 | 1062.0 | 175.2% | 10843.3 | n/a |
| Alginate | 0.42 | 961.4 | 27.5 | 1547.4 | n/a |
| Almond Nut Shell Powder | 1.81 | 1932.0 | 10.8 | 1208.7 | 250 |

TABLE 1-continued

| Sample Description | Sample Thickness (mm) | Peak Load (gF) | Peak Stretch (%) | Peak Energy (g/cm) | Particle Size (μm) |
|---|---|---|---|---|---|
| Cellulose | 1.66 | 2340.1 | 4.6 | 512.0 | 20 |
| Corn starch | 1.46 | 1720.2 | 10.2 | 273.6 | 0.1-0.8 |
| Fava | 1.85 | 2096.2 | 9.7 | 1137.0 | 110 |
| Kenaf | 3.31 | >100 N load | not tested | not tested | 250 |
| Rice | 1.58 | 1727.3 | 9.5 | 910.4 | 180 |
| Wheat Flour | 0.82 | 764.4 | 4.8 | 193.2 | 60 |
| Teff | 1.62 | 1782.5 | 4.0 | 374.8 | 180 |

Figure 1:
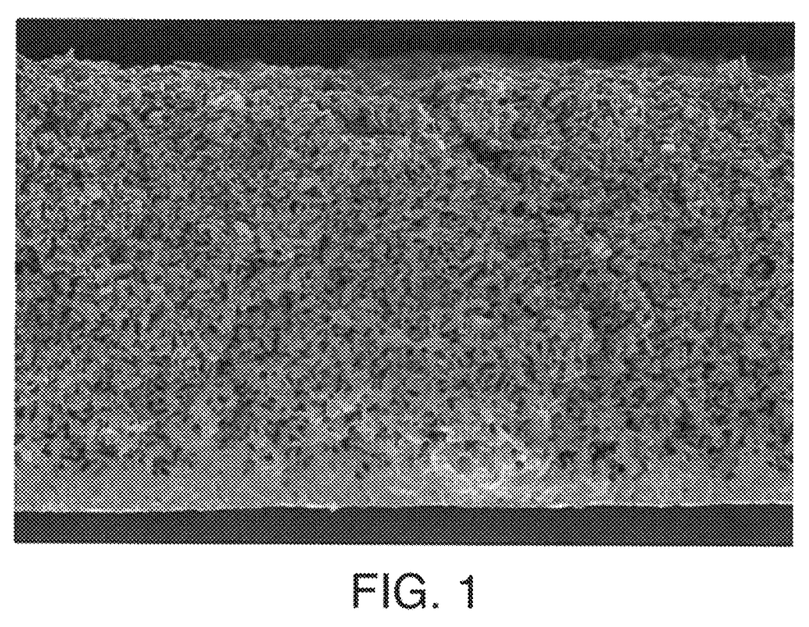
FIG. 1 is a cross-sectional view of an embodiment of the porous absorbent structure of the present invention.
Figure 2:
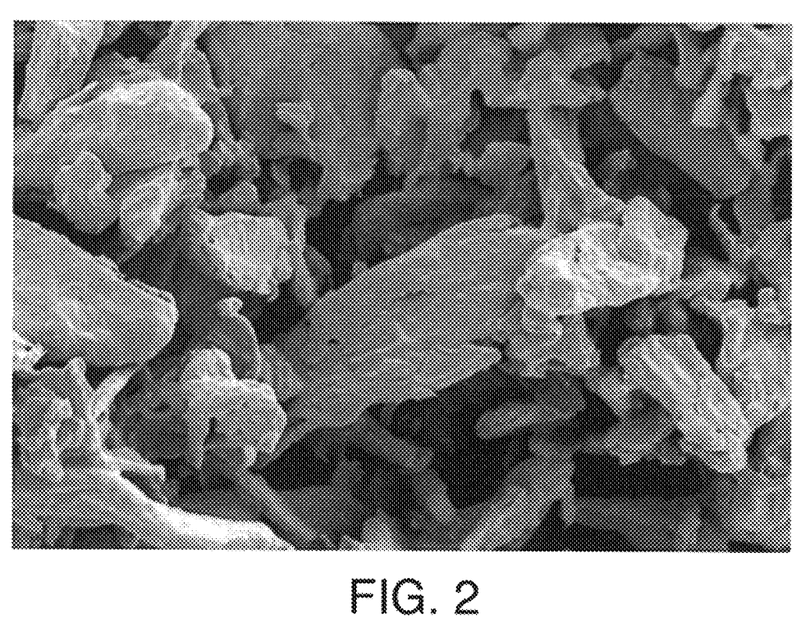
FIG. 2 is an enlarged cross-sectional view of an embodiment of the porous absorbent structure of the present invention.
Figure 3:
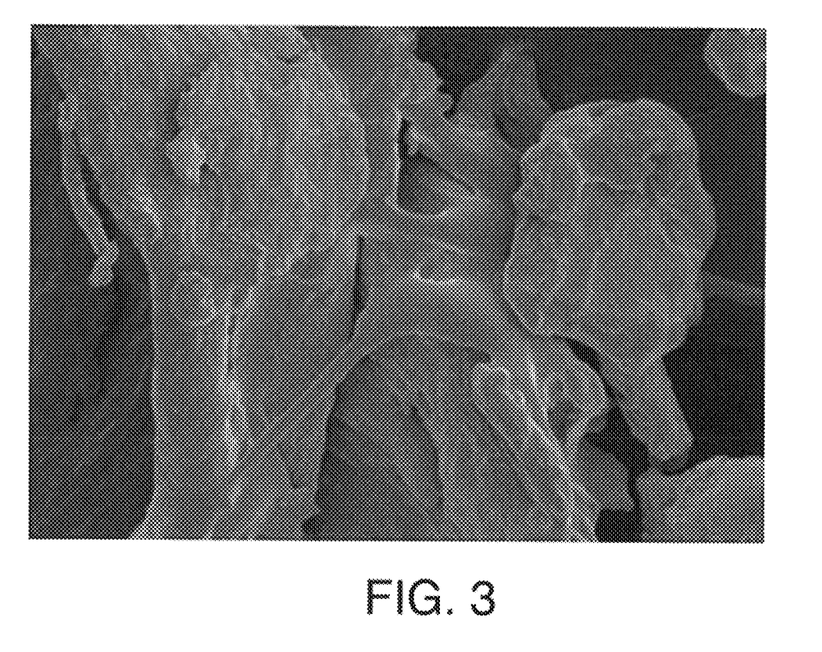
FIG. 3 is a close up view of an embodiment of the porous absorbent structure of the present invention.
Figure 4:
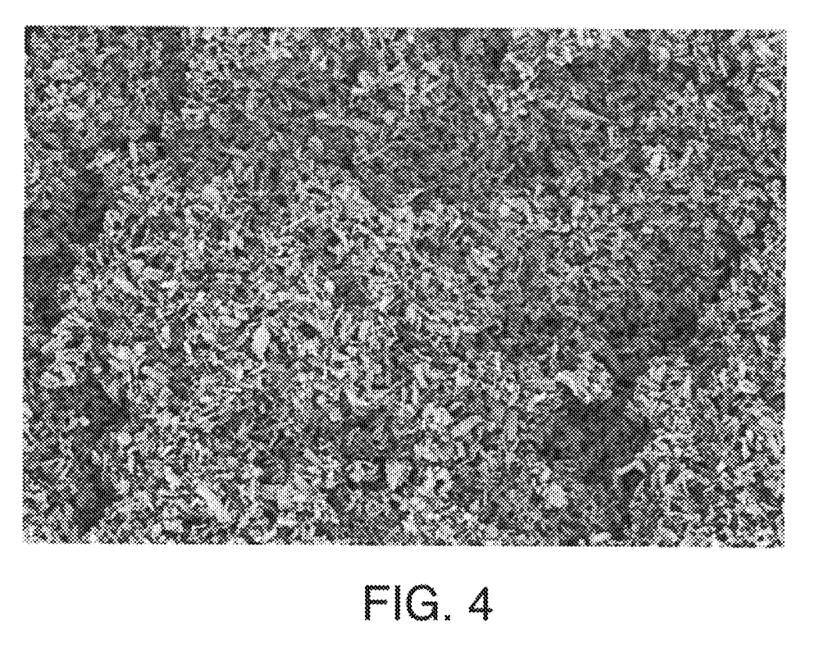
FIG. 4 is a view of the top surface of the porous absorbent structure of the present invention.
Figure 5:
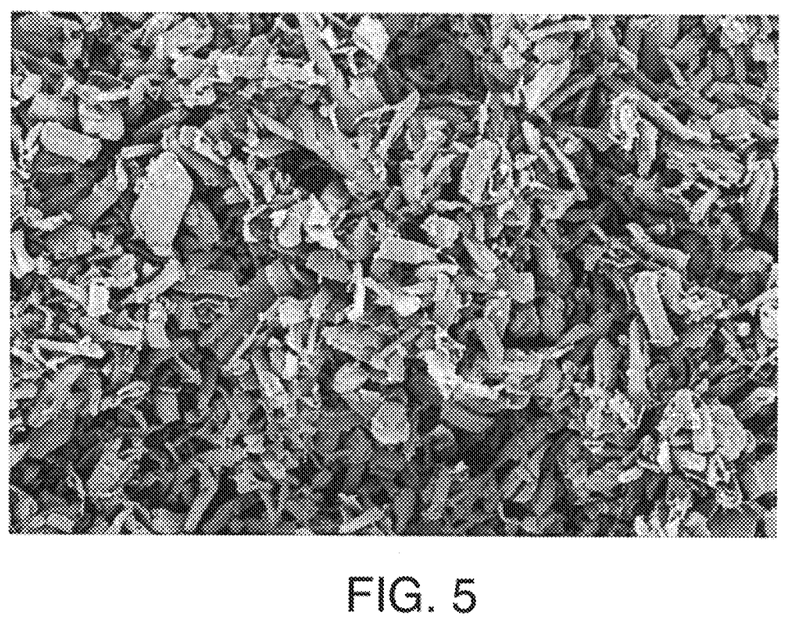
FIG. 5 is an enlarged view of the top surface of the porous absorbent structure of the present invention.

FIGS. 1-5 are views of the porous absorbent structure formed with micronized cellulose. FIG. 1 is a scanning electron micrograph image of a cross-section of the porous absorbent structure formed with micronized cellulose. FIGS. 2 and 3 are enlargements of portions of the cross-sectional view. As can be seen in FIGS. 2 and 3, the absorbent particles are substantially coated with superabsorbent polymer material, which also acts to bind the absorbent particles together. The porosity of the porous absorbent structure is created by the evaporating water, which also permits the superabsorbent polymer material to effectively cross-link.

It is believed that, when the porous absorbent structure comes into contact with a fluid, the superabsorbent polymer material is the first to absorb the fluid. Although the absorbent particles may, in some embodiments, be substantially or completely covered by superabsorbent polymer material, the absorbent particles still contribute to the absorptive capacity of the porous absorbent structure as they are positioned to absorb fluid from the superabsorbent polymer material.

The samples formed with the particles listed in Table 2 were formed in the same manner as the samples listed in Table 1. The porous absorbent structure formed with Arizona sand (available from CR Minerals Co., Golden, Colo., U.S.A.) and pumice (available from Charles B. Crystal Co., New York, N.Y., U.S.A.) demonstrated good integrity and strength. The surface of these porous absorbent structures was similar to a fine-grit sandpaper. The bentonite particles (available from Acros Organics, Fair Lawn N.J., U.S.A) formed a material with quite high peak load values. The diatomaceous earth (available from Aldrich Chemical Company, Milwaukee Wis., U.S.A.) and silica samples (Sigma-Aldrich Chemical Co. Milwaukee Wis., U.S.A.) formed structures that were not able to be tested due to their lack of integrity. One possible reason for this is that these particles provided too much cross-linking capability within the example.

TABLE 2

| Sample Description | Sample Thickness (mm) | Peak Load (gF) | Peak Stretch (%) | Peak Energy (g/cm) | Particle Size (μm) |
|---|---|---|---|---|---|
| Arizona sand | 1.14 | 2023.1 | 7.3 | 740.6 | 30 |
| Bentonite | 1.46 | >100 N | not tested | not tested | 75 |
| Chalk | 1.62 | 1028.3 | 80.5 | 1722.9 | 30 |
| Diatomaceous earth | 1.46 | Brittle | n/a | n/a | 3 |
| Pumice | 1.76 | >100 N | 37.1 | 957.3 | 35 |
| Silica | 1.81 | brittle | n/a | n/a | 300-600 |
| Silica (nanoparticle) | 1.50 | brittle | n/a | n/a | 0.014 |

Based on the above samples, preferred embodiments of the present invention may have a Peak Energy of at least about 150 g/cm, and may preferably have a Peak Energy of at least about 500 g/cm.

The porous absorbent structure may be used in a variety of absorbent products, such as, for example, bandages, training pants, diapers, diaper pants, wipes, feminine hygiene products, swimwear, incontinence products, absorbent toweling, other personal care or health care garments, including medical garments, or the like. Such absorbent products may include an outer cover adapted to be secured to a person. On an inside surface of the outer cover, the porous absorbent structure may be formed or may be applied once formed.

It should be appreciated by those skilled in the art that various modifications and variations may be made to features of the dispenser described herein, particularly to the mechanical and control circuitry aspects of the dispenser, without departing from the scope and spirit of the invention. It is intended that the invention include all such variations.

What is claimed is:

1. A method of forming a porous absorbent structure comprising the steps of:
   providing a superabsorbent polymer material having a viscosity of less than about 10,000 cps and having less than about 1000 parts per million residual monoethylenically unsaturated monomer;
   adding absorbent particles into the superabsorbent polymer material to form a mixture such that the ratio by weight of superabsorbent polymer material to absorbent particles is greater than 3:1;
   spraying the mixture of superabsorbent polymer material and absorbent particles onto a form; and
   drying the mixture to produce a porous absorbent structure substantially conforming to the shape of the form.

2. The method of claim 1 wherein the form is at least a portion of a human body.

3. The method of claim 1 wherein the form is selected from the group comprising: a nonwoven material, a woven material, paper, a film or a combination thereof.

4. A method of forming a porous absorbent structure comprising the steps of:
   providing a superabsorbent polymer material having a viscosity of less than about 10,000 cps;
   adding absorbent particles into the superabsorbent polymer material to form a mixture such that the ratio by weight of superabsorbent polymer material to absorbent particles is greater than 3:1;
   spraying the mixture of superabsorbent polymer material and absorbent particles onto a form;
   drying the mixture to produce a porous absorbent structure substantially conforming to the shape of the form; and
   removing the porous absorbent structure from the form.

5. The method of claim 1 wherein the monoethylenically unsaturated monomer is acrylic acid.

6. The method of claim 1 wherein the absorbent particles are organic particles.

7. The method of claim 1 wherein the absorbent particles have an average ratio of length to width of less than about 5.

8. The method of claim 1 wherein the step of drying the mixture further includes drying the mixture to induce cross-linking in the superabsorbent polymer material and to produce a porous absorbent structure substantially conforming to the shape of the form.

9. The method of claim 1 wherein the absorbent particles have an average length of greater than 20 microns.

10. The method of claim 1 wherein the ratio by weight of superabsorbent polymer material to absorbent particles in the mixture is less than about 6:1.

11. The method of claim 10 wherein the ratio by weight of superabsorbent polymer material to absorbent particles in the mixture is greater than 3.5:1.

12. The method of claim 1 wherein the step of adding absorbent particles into the superabsorbent polymer material further includes wherein the superabsorbent polymer material substantially coats the absorbent particles.

13. A porous absorbent structure formed by the process comprising the steps of:
provingg a superabsorbent polymer material having a viscosity of less than about 10,000 cps and having less than about 1000 parts Per million residual monoethylenically unsaturated monomer;
adding absorbent particles into the superabsorbent polymer material to form a mixture, wherein the ratio by weight of superabsorbent polymer material to absorbent particles in the mixture is greater than 3:1 and less than about 6:1;
applying the mixture of superabsorbent polymer material and absorbent particles to a form; and
drying the mixture to produce a porous absorbent structure substantially conforming to the shape of the form.

14. The porous absorbent structure of claim 13 wherein the form is at least a portion of a human body.

15. The porous absorbent structure of claim 13 wherein the form is selected from the group comprising: a nonwoven material, a woven material, paper, a film or a combination thereof.

16. A porous absorbent structure formed by the process comprising the steps of:
providing a superabsorbent polymer material having a viscosity of less than about 10,000 cps;
adding absorbent particles into the superabsorbent polymer material to form a mixture, wherein the ratio by weight of superabsorbent polymer material to absorbent particles in the mixture is greater than 3:1 and less than about 6:1;
applying the mixture of superabsorbent polymer material and absorbent particles to a form;
drying the mixture to produce a porous absorbent structure substantially conforming to the shape of the form; and
removing the porous absorbent structure from the form.

17. A porous absorbent structure comprising:
absorbent particles;
a superabsorbent polymer material substantially coating the absorbent particles and connecting the absorbent particles into a porous absorbent network; and
wherein the ratio by weight of the superabsorbent polymer material to the absorbent particles in the porous absorbent structure is greater than 1:1 and less than 1.5:1 and wherein the superabsorbent polymer material has less than about 1000 parts per million residual monoethylenically unsaturated monomer.

18. The porous absorbent structure of claim 17 wherein the weight ratio of the superabsorbent polymer material to the absorbent particles is 1.1:1.

19. A porous absorbent structure comprising:
absorbent particles;
a superabsorbent polymer material substantially coating the absorbent particles and connecting the absorbent particles into a porous absorbent network; and
wherein the ratio by weight of the superabsorbent polymer material to the absorbent particles in the porous absorbent structure is greater than 1:1 and less than 1.5:1 and wherein the porous absorbent structure has a Peak Stretch of at least about 10%.

20. A porous absorbent structure comprising:
absorbent particles;
a superabsorbent polymer material substantially coating the absorbent particles and connecting the absorbent particles into a porous absorbent network; and
wherein the ratio by weight of the superabsorbent polymer material to the absorbent particles in the porous absorbent structure is greater than 1:1 and less than 1.5:1 and wherein the porous absorbent structure has a Peak Energy of at least about 150 g/cm.

21. The porous absorbent structure of claim 17 further comprising a nonwoven material.

22. The porous absorbent structure of claim 21 wherein the nonwoven material and porous absorbent structure form a wiper.

23. An absorbent article comprising:
an outer cover adapted to be secured to a person, the outer cover having an inner side;
a porous absorbent structure comprising
absorbent particles and
a superabsorbent polymer material substantially coating the absorbent particles and connecting the particles into a porous network to form an absorbent core that is positioned on the inner side of the outer cover, wherein the ratio by weight of the superabsorbent polymer material to the absorbent particles in the porous absorbent structure is greater than 0.8:1 and less than 1.4:1 and wherein the superabsorbent polymer material has less than about 1000 parts per million residual monoethylenically unsaturated monomer.

24. An absorbent article comprising:
an outer cover adapted to be secured to a person, the outer cover having an inner side;
a porous absorbent structure comprising
absorbent particles and
a superabsorbent polymer material substantially coating the absorbent particles and connecting the particles into a porous network to form an absorbent core that is positioned on the inner side of the outer cover, wherein the ratio by weight of the superabsorbent polymer material to the absorbent particles in the porous absorbent structure is greater than 0.8:1 and less than 1.4:1 and wherein the porous absorbent structure has a Peak Stretch of at least about 10%.

* * * * *